United States Patent [19]

Matsuoka et al.

[11] Patent Number: 5,030,387

[45] Date of Patent: Jul. 9, 1991

[54] ORGANIC CONDUCTIVE COMPLEX

[75] Inventors: Masaru Matsuoka, Nara; Teijiro Kitao; Yo Shimizu, both of Osaka, all of Japan

[73] Assignee: Sumitomo Electric Industries Ltd., Osaka, Japan

[21] Appl. No.: 371,902

[22] Filed: Jun. 27, 1989

[30] Foreign Application Priority Data

Jun. 27, 1988 [JP] Japan .................... 63-158695

[51] Int. Cl.$^5$ .................... F21V 9/04; G02B 5/02; A01B 12/00; C07C 50/02
[52] U.S. Cl. .................... 252/582; 252/589; 505/1; 552/234; 552/235; 552/238; 552/243; 552/282; 552/264; 552/267; 552/303
[58] Field of Search ............ 260/378, 379, 380, 381, 260/369; 252/299.01, 299.1, 299.3, 582, 589; 552/303, 234, 235, 238, 243, 262, 264, 267; 505/1

[56] References Cited

U.S. PATENT DOCUMENTS

| | | | |
|---|---|---|---|
| 1,976,167 | 10/1934 | Grossmann | 260/380 |
| 3,975,285 | 8/1978 | Ohnishi et al. | 252/299.3 |
| 4,201,638 | 5/1980 | Wah et al. | 260/396 |
| 4,232,950 | 11/1980 | Benham | 252/299.1 |
| 4,478,753 | 10/1984 | Hotte et al. | 260/396 N |
| 4,606,861 | 8/1986 | Ohg et al. | 260/351 |
| 4,769,448 | 9/1988 | Heeger et al. | 552/203 |
| 4,773,743 | 9/1980 | Choe et al. | 260/396 N |

FOREIGN PATENT DOCUMENTS 0061264 3/1982 European Pat. Off. .

*Primary Examiner*—C. Warren Ivy
*Assistant Examiner*—Raymond Covington
*Attorney, Agent, or Firm*—Sughrue, Mion, Zinn, Macpeak & Seas

[57] ABSTRACT

An organic conductive complex comprising an electron donor and an electron acceptor, the electron donor being an anthraquinone derivative represented by formula (1):

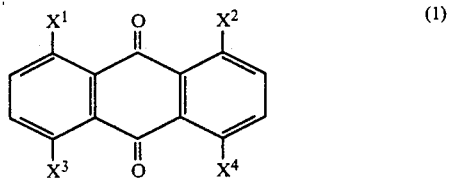

wherein $X^1$, $X^2$, $X^3$ and $X^4$, which may be the same or different, each represents an electron donating group.

3 Claims, 4 Drawing Sheets

ORGANIC CONDUCTIVE COMPLEX

BACKGROUND OF THE INVENTION

The present invention relates to an organic conductive complex, more particularly, to an organic conductive complex that is advantageously used for a thermal switch, a thermoelectric elemental device, a galvanic cell, a diode switch, a thermoelectric and electrothermal modulation device, etc., and has the potential to be used in such applications as superconducting materials, third-order nonlinear materials and photoconductive materials.

Synthetic metals that have been proposed as metal substitutes include not only conductive polymers and graphite compounds but also organic conductive complexes (e.g. ion radical salts and intermolecular charge-transfer complexes) that are composed of electron donors and acceptors. In organic conductive complexes, electrons are transferred from the electron donor to the acceptor and are stabilized to form a stable complex; the resulting high intramolecular and intermolecular mobility of electrons (i.e. delocalization) contributes to conducting or semiconducting electric behavior.

Electron donors that are capable of forming organic complexes having high conductivity may be exemplified by bisethylenedithia-tetrathiafulvalene (BEDTTTF) (as described, e.g., in *Chem. Lett.*, 1985, pp. 1293 and *Pis'ma Zh. Eksp. Teor. Fiz.*, vol. 40, pp. 387 (1984)) and tetrathiafulvalene (TTF) (as described, e.g., in *Phys. Rev.*, vol. B13, pp. 5105 (1976) and *Phys. Soc. Japan*, vol. 41, pp. 351 (1976)). Illustrative electron acceptors include 7,7,8,8-tetracyanoquinodimethane (TCNQ) tetracyanoethylene (TCNE). All of these compounds have planar molecular structures and it is theorized that within the crystal of an organic conductive complex, their planes are alternately stacked, with adjacent planes facing substantially parallel to each other, so that $\pi$ electrons in the electron donor will be transferred to the $\pi$ orbital in the electron acceptor, thereby creating the "delocalized state" mentioned above.

While various compounds are used as dyes, anthraquinone derivatives have substantially planar molecular structures of the same type as those possessed by the electron donors and acceptors described above. The present inventors thus theorized that by selecting proper substituents, anthraquinone derivatives useful as electron donors or acceptors in the synthesis of organic conductive complexes might be obtained and on the basis of this assumption, they reviewed various anthraquinone derivatives to search for the compounds that would be as effective as BEDT-TTF, TTF, TCNQ, TCNE, etc. As a result, the present inventors found that an anthraquinone derivative having an electron donating group on the 1, 4, 5 and 8 positions of 9, 10-anthraquinone would be useful as an electron donor in an organic conductive complex.

SUMMARY OF THE INVENTION

The present invention has been accomplished on the basis of this finding and an object thereof is to provide a novel and useful organic conductive complex that is advantageously used for a thermal switch, a thermoelectric elemental device, a galvanic cell, a diode switch, a thermoelectric and electrothermal modulation device, etc., and has the potential to be used in such applications as superconducting materials, third-order nonlinear optical materials and photoconductive materials.

Other objects and effects of the present invention will be apparent from the following description.

The objects of the present invention can be attained by an organic conductive complex comprising an electron donor and an electron acceptor, said electron donor being an anthraquinone derivative represented by formula (1):

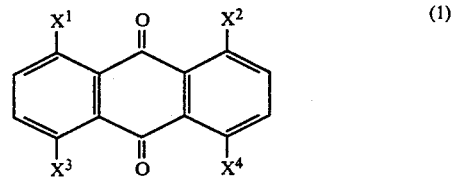

$X^1$, $X^2$, $X^3$ and $X^4$, which may be the same or different, each represents an electron donating group.

DETAILED DESCRIPTION OF THE INVENTION

Figure 1:
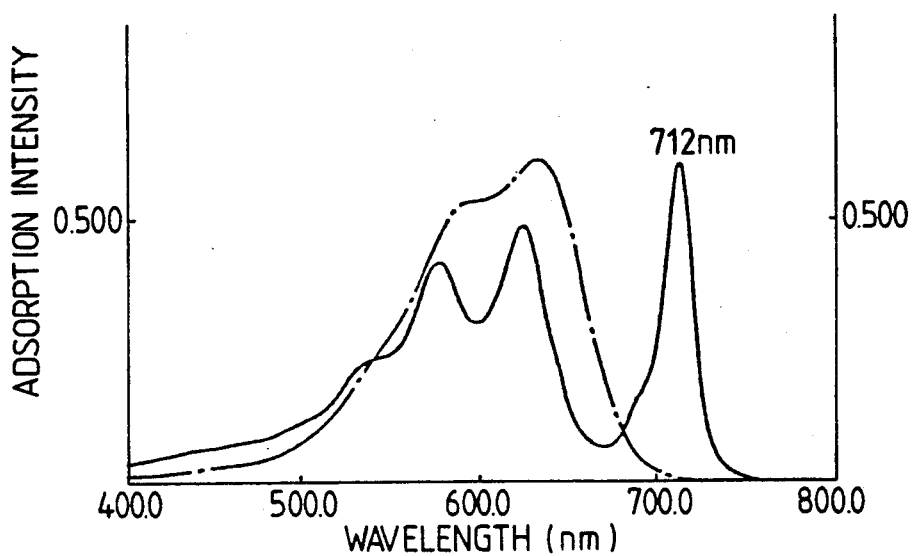
FIGS. 1 to 3 are diagrams showing absorption spectra in the near infrared and visible ranges for the organic conductive complexes prepared in Examples 2 to 4, respectively.

The antraquinone derivatives represented by formula (1) have substantially planar molecular structures as is suggested by the formula. In addition, they have a substantially symmetric electric structure with electron donating groups $X^1$ to $X^4$ being present on the 1, 4, 5 and 8 positions of 9, 10-anthraquinone. Because of this structure, the anthraquinone derivatives of formula (1) are useful as electron donors as are BEDT-TTF and TTF which are known electron donors. Examples of the electron donating substituents $X^1$ to $X^4$ that provide anthraquinone derivatives having the properties described above include an amino group, a hydroxyl group, a halogen atom, an alkyl group, a thiol group, an alkylthio group, an alkoxy group, an acetoamino group, a monoalkylamino group, a dialkylamino group, etc., and a particularly preferred example is 1,4,5,8-tetraaminoanthraquinone (TAAQ) where every one of the substituents $X^1$ to $X^4$ is an amino group.

The organic conductive complex of the present invention has an electron acceptor in addition to the anthraquinone derivative of formula (1) serving as an electron donor, and illustrative electron acceptors that may be used include not only the TCNQ and TCNE that are already mentioned but also other known compounds such as 5-nitro-2,3-dicyano-1,4-naphthoquinone (NDCNQ) and 2,3-dicyano-1,4-naphthoquinone (DCNQ). These electron acceptors may be used either on their own or as admixtures.

The anthraquinone derivative of formula (1) which serves as an electron donor will combine with a suitable electron acceptor of the type mentioned above for example to form the organic conductive complex of the present invention. As in the case of known organic conductive complexes, it can be understood that the electron donor and acceptor both having a substantially planar molecular structure are stacked in the crystal of the organic conductive complex of the present invention, with adjacent planar surfaces being opposed substantially parallel to each other, so that x electrons in the electron donor are transferred to the x orbital in the electron acceptor, thereby contributing conducting electric behavior. In particular, an organic conductive complex using TAAQ as an anthraquinone derivative of formula (1) allows for extensive charge transfer, so that an ionic intermolecular compound (ion radical salt) is formed between a nearly positive monovalent electron donor and a nearly negative monovalent electron acceptor, thus contributing a higher conductivity. In addition, the anthraquinone derivative of formula (1) which is of an intramolecular charge-transfer type having an electron accepting carbonyl group in the center of the molecule and being surrounded with electron donating substituents $X^1$ to $X^4$ will yield an even higher degree of electron donating quality and enables the radical cation species to be present in a more stable state. Hence, the organic conductive complex of the present invention is advantageously used for a thermal switch, a thermoelectric elemental device, a galvanic cell, a diode switch, a thermoelectric and electrothermal modulation device, etc., and has the potential to be used as a superconducting material with a proper acceptor molecule.

Because of its strong radical ionic property, the organic conductive complex of the present invention, in particular, that containing TAAQ as an anthraquinone derivative of formula (1), can also be used as a valuable cubic nonlinear optical material. In addition, the organic conductive complex of the present invention also has the potential to be used as a photoconductive material if it is engineered as a semiconductor by properly selecting the electron donating groups $X^1$ to $X^4$.

The following examples are provided for the purpose of further illustrating the present invention but are in no way to be taken as limiting.

EXAMPLE 1

A crystal of TAAQ commercially available as a dye was dissolved in nitrobenzene under heating, and the component (mainly the dispersant) that was insoluble in nitrobenzene was filtered off while hot. The filtrate was cooled to recrystallize TAAQ. These procedures were repeated four times. Using pyridine, the resulting TAAQ crystal was subjected to three cycles of recrystallization in the same manner as in the case of nitrobenzene, thereby removing another impure species. The so treated TAAQ crystal was purified by sublimation at 180° C. and at 2 to 5 mmHg, and the purified crystal was dissolved in distilled methylene chloride (100 ml per 0.1 g of the crystal) to form a solution. In a separate step, a crystal of TCNQ, which was purified in a similar manner as in the case of TAAQ and was measured in an amount equimolar to the TAAQ crystal, was also dissolved in distilled methylene chloride (100 ml per 0.1 g of the crystal) to form a solution. When the two solutions thus formed were simultaneously added dropwise to methylene chloride (50 ml), deep blue, tiny crystals precipitated. These crystals were recovered from the methylene chloride by filtration, washed with methylene chloride (50 ml), and transferred onto dry filter paper where they were dried with air. By subsequent vacuum drying, a sample of organic conductive complex was prepared.

EXAMPLE 2 TO 4

Additional samples of organic conductive complex in the form of deep blue, tiny crystals were prepared by the same manner as in Example 1 except that the TCNQ crystals were replaced by crystals of TCNE (Example 2), NDCNQ (Example 3) and DCNQ (Example 4) in amounts that were equimolar to the TAAQ crystal.

Measurement of conductivity

The sample of organic conductive complex prepared in Example 1 was put into a pressurizing mold and pressed at 200 kg/cm² for 5 minutes at room temperature to prepare a bar-shaped test piece (0.06 $cm^T \times$ 0.3 $cm^W \times$ 2 $cm^L$). Two copper leads spaced apart by a distance of 0.28 cm in a direction perpendicular to the length of the test piece were attached to the substantially central portion of its major side (0.3 cm × 2 cm) by means of silver paste. Two additional copper leads were attached to the opposite sides of the first set of copper leads by means of silver paste.

The so prepared test piece was placed in a sealable measuring chamber, which was substituted with helium gas. Thereafter, with a constant current of 1 mA being applied to the two outer Cu leads, the voltage (mV) between the two inner Cu leads was measured by the four-terminal method. The conductivity (S/cm) of the sample under test was calculated from the measured voltage (mV) and the value of applied current (mA). The result is shown in Table 1.

The sample of organic conductive complex prepared in Example 2 was also molded under pressure into a bar measuring 0.1 cm thick, 0.3 cm wide and 2 cm long. After attaching four copper leads in the same manner as described above, the conductivity of the test piece was measured by the four-terminal method. In the case of this test piece, the two inner Cu leads for voltage measurement were kept apart by a distance of 0.2 cm and a constant current of 0.01 mA was applied to the two outer Cu leads. The result of measurement is shown in Table 1.

TABLE 1

| Sample | Electron Acceptor | Conductivity (S/cm) |
|--------|-------------------|---------------------|
| Example 1 | TCNQ | 20 |
| Example 2 | TCNE | $7 \times 10^{-2}$ |

The data in Table 1 shows that both the samples of organic conductive complex prepared in Examples 1 and 2 exhibit high conductivity at room temperature in comparison to conventional products.

Characterization of organic conductive complexes

Figure 2:
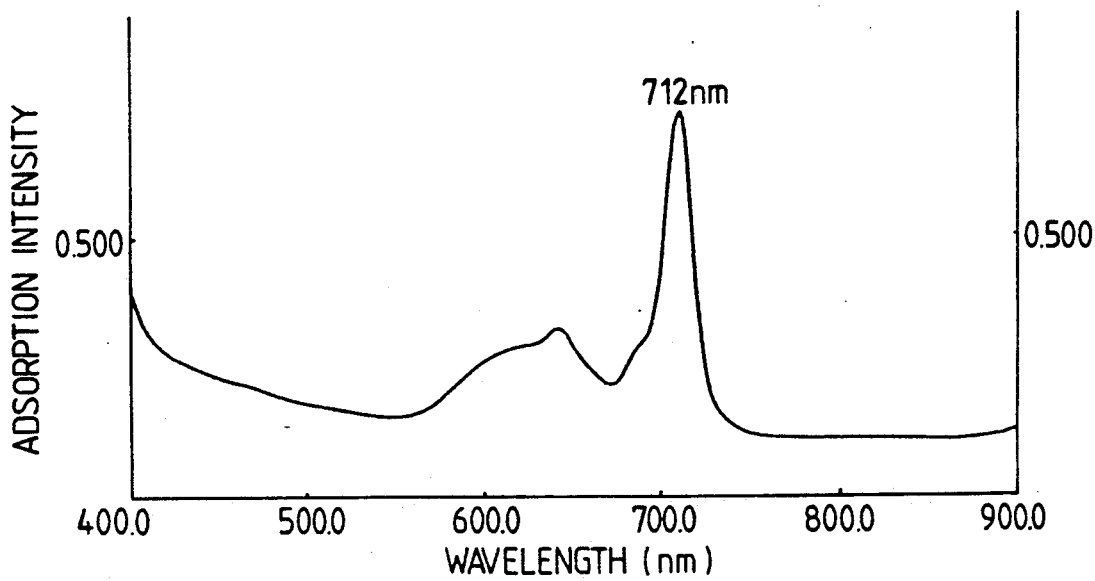
Figure 3:
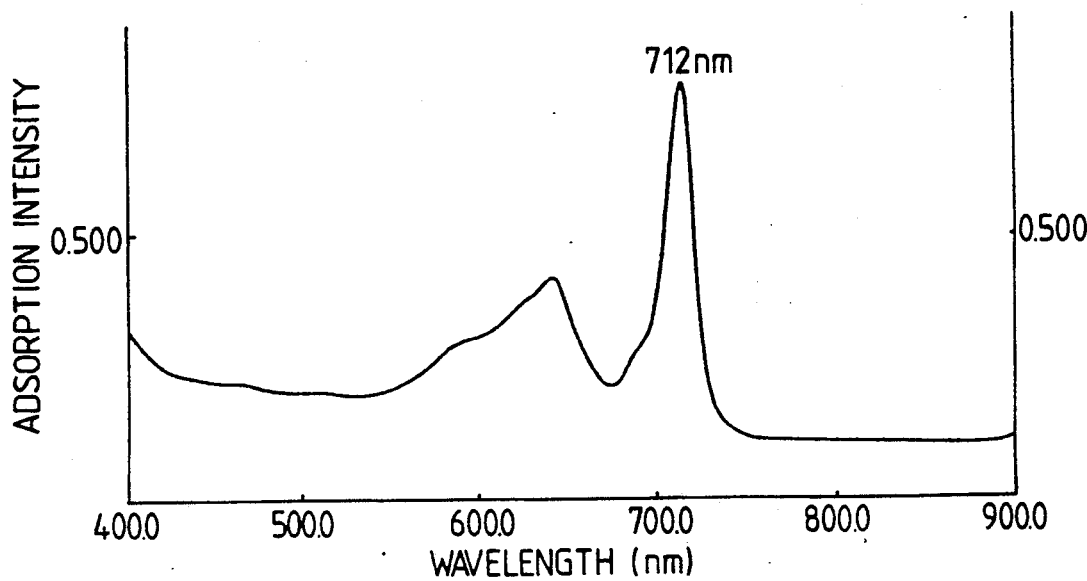
Figure 4:
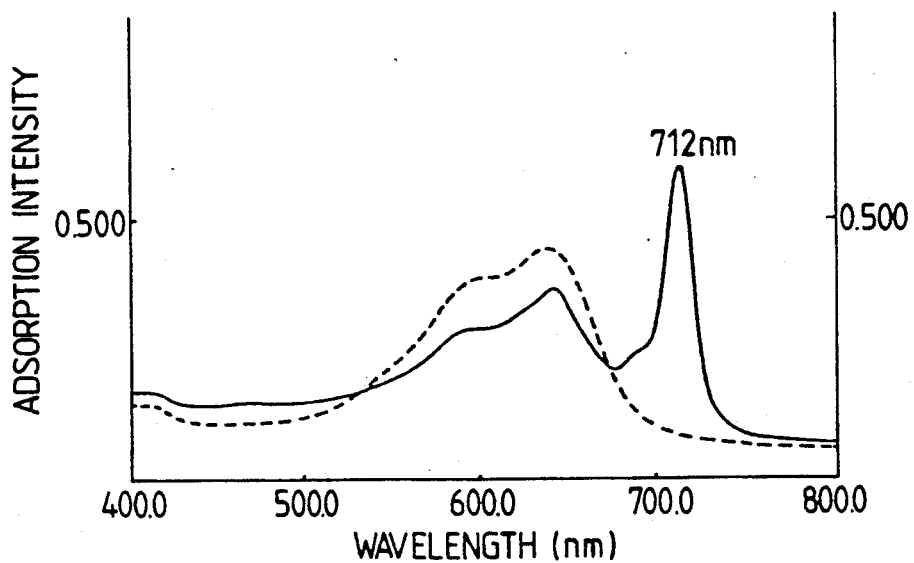
FIG. 4 is a diagram showing the absorption spectra of two solutions of the organic conductive complex prepared in Example 2, one containing pyrogallol and the other containing no pyrogallol.

The samples of organic conductive complex prepared in Examples 2 to 4 were dissolved in ethanol and the absorption spectra of the resulting solutions in the near infrared and visible regions were measured. The results are shown in FIGS. 1 to 3. The absorption spectrum of a solution having only the TAAQ crystal dissolved in ethanol is also shown by a one-long-and-one-short dashed line in FIG. 1. FIG. 4 shows two absorption spectra, one represented by a dashed line and referring to the ethanol solution of the organic conductive complex prepared in Example 2 to which was added pyrogallol more electron donating than TAAQ, and the other spectrum represented by a solid line and referring to the ethanol solution of the same organic conductive complex to which no pyrogallol was added.

Figure 5:
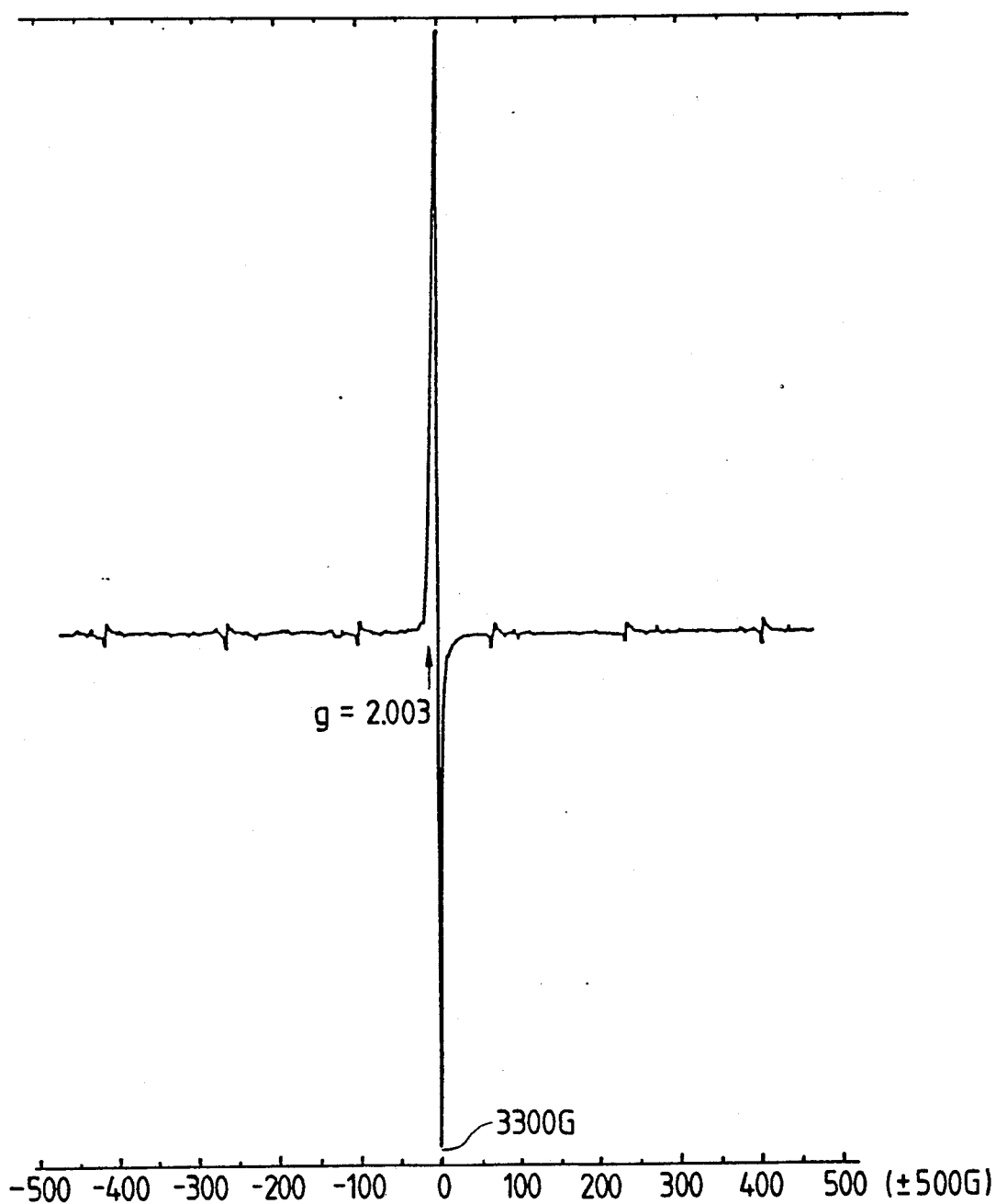
FIGS. 5 and 6 are the ESR (electron spin resonance) spectra of the organic conductive complexes prepared in Examples 1 and 2, respectively.
Figure 6:
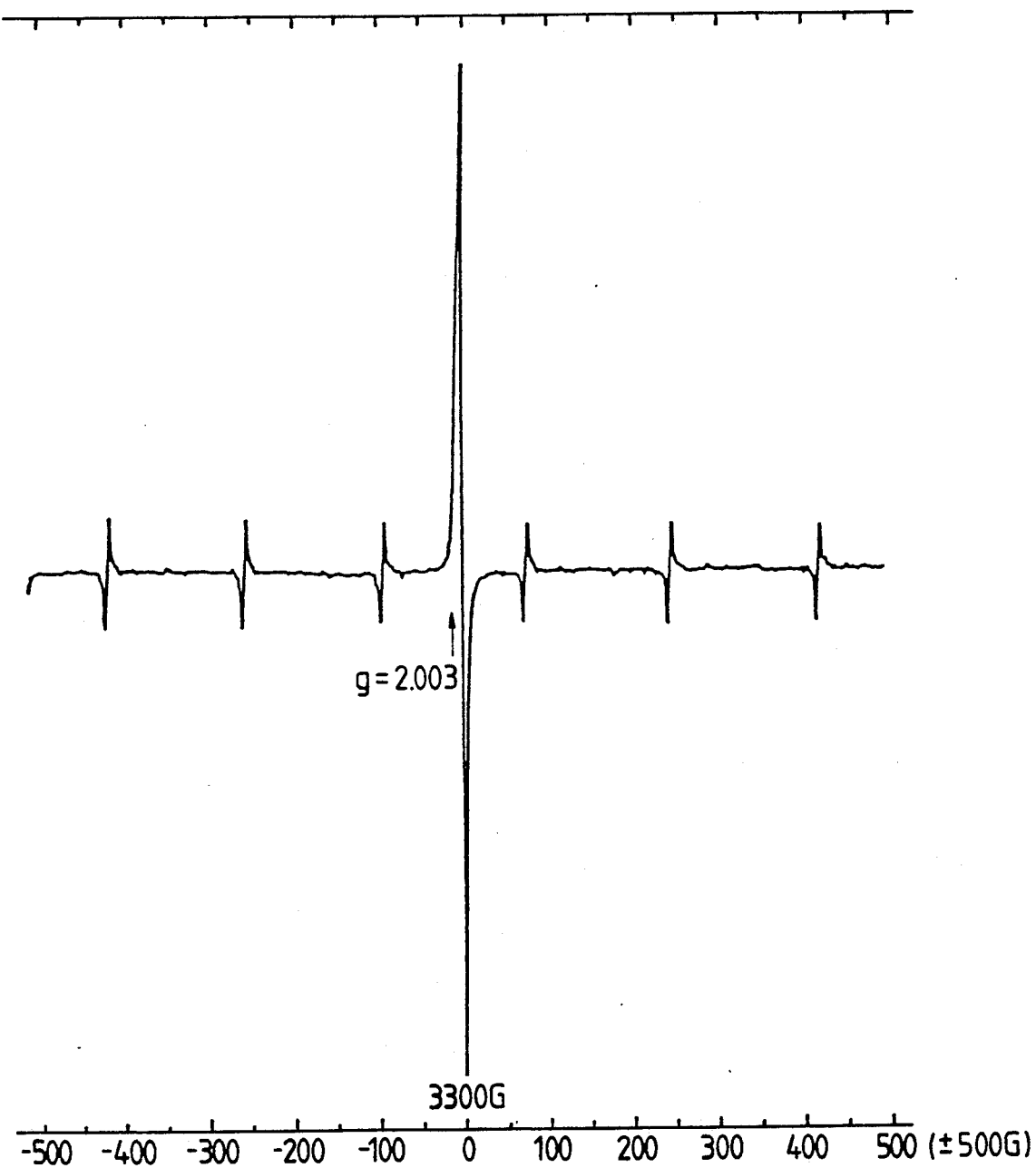

Electron spin resonance (ESR) spectroscopy was conducted on the samples of organic conductive complex of Examples 1 and 2 using manganese dioxide as the standard material. The resulting ESR spectra are shown in FIGS. 5 and 6. The conditions of ESR spectroscopy were as follows:

| Sample weight | 0.0001 g |
| --- | --- |
| Temperature | 20° C. |
| RF field | 3,300 G ± 500 G |
| Sweep time | 4.0 min. |
| Modulation | 100 kHz, 2.0 G |
| Amplitude | 1.0 × 100 |
| Response | 0.01 sec. |
| Output | 1.0 mW |
| Crystal current | 0.1 mA |
| Frequency | 9.56 GHz |

Using a CH coder, the samples of organic conductive complex prepared in Examples 1 to 4 were subjected to elemental analysis for C, H and N, and the results are shown in Table 2 together with the calculated values (%) of C, H and N that should be present when the electron donor TAAQ forms a 1/1 complex with a respective electron acceptor.

TABLE 2

| Sample | Element | Elemental analysis (%) | |
| --- | --- | --- | --- |
| | | Cal'd | Found |
| Example 1 | H | 3.41 | 3.02 |
| | C | 66.10 | 65.37 |
| | N | 23.72 | 23.30 |
| Example 2 | H | 3.05 | 3.16 |
| | C | 60.61 | 59.89 |
| | N | 28.27 | 28.86 |
| Example 3 | H | 2.90 | 2.65 |
| | C | 58.89 | 57.69 |
| | N | 18.80 | 17.98 |
| Example 4 | H | 3.38 | 3.07 |
| | C | 65.54 | 64.85 |
| | N | 17.64 | 17.31 |

As FIGS. 1 to 3 show, a characteristic absorption peak was observed with all the samples of organic conductive complex prepared in Examples 2 to 4 and absorption wavelength of that peak was the same (712 nm) irrespective of the type of electron acceptor used. As FIG. 1 shows, this characteristic absorption peak was not observed with TAAQ alone. As is clear from FIG. 4, this characteristic absorption peak disappeared when pyrogallol which was a stronger electron donor than TAAQ was added to the complex. Based on these observations, it was understood that the absorption peak at 712 nm was due to charge transfer between TAAQ and each of the electron acceptors used.

In the ESR spectroscopy of the samples prepared in Examples 1 and 2, strong resonance due to unpaired electrons was observed on the position of g=2.003 and this result was substantially the same irrespective of the type of electron acceptor used. Hence, it was understood that radicals were generated between TAAQ and each of the electron acceptors on account of charge transfer.

The data in Table 2 shows substantial agreement between the calculated and found values of C, H and N for each of the organic conductive complexes prepared in Examples 1 to 4, and this points to the fact that the electron donor TAAQ and an electron acceptor were present at the molar ratio of 1/1 in each of the complexes.

The above results show that TAAQ formed a 1/1 radical ion salt with an electron acceptor in each of the organic conductive complexes prepared in Examples 1 to 4. 1

As described on the foregoing pages, the organic conductive complex of the present invention which contains an anthraquinone derivative of the general formula (1) as an electron donor exhibits higher conductivity than the conventional products, so that it is advantageously used for a thermal switch, a thermoelectric elemental device, a galvanic cell, a diode switch, a thermoelectric and electrothermal modulation device, etc., and has the potential to be used in various applications including superconducting materials, third-order nonlinear optical materials and photoconductive materials.

While the invention has been described in detail and with reference to specific examples thereof, it will be apparent to one skilled in the art that various changes and modifications can be made therein without departing from the spirit and scope thereof.

What is claimed is:

1. An organic conductive complex comprising an electron donor and an electron acceptor, said electron donor being an anthraquinone derivative represented by formula (1):

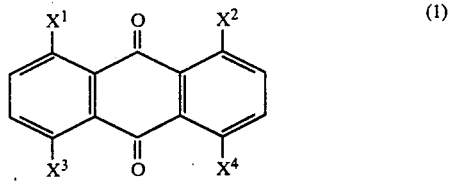

wherein $X^1$, $X^2$, $X^3$ and $X^4$, which may be the same or different, each represents an electron donating group, and wherein said electron acceptor is at least one compound selected from the group consisting of 7,7,8,8-tetracyanoquinodimethane, tetracyanoethylene, 5-nitro-2,3-dicyano-1,4-napthoquinone and 2,3-dicyano-1,4-naphthoquinone.

2. An organic conductive ocmplex as claimed in claim 1, wherein $X^1$, $X^2$, $X^3$ and $X^4$ each represents an amino group, an hydroxy group, an halogen atom, an alkyl group, a thiol group, an alkylthio group, an alkoxy group, an acetoamino group, a monoalkylamino group or a dialkylamino group.

3. An organic conductive complex as claimed in claim 2, wherein said electron donating groups represented by $X^1$, $X^2$, $X^3$ and $X^4$ each represents an amino group.

* * * * *